(12) United States Patent
De Mayo et al.

(10) Patent No.: US 10,357,236 B2
(45) Date of Patent: Jul. 23, 2019

(54) ELEVATION DEVICE FOR MODULAR DISTRACTOR FOR USE IN ANKLE AND LEG SURGERY

(71) Applicant: INNOVATIVE MEDICAL PRODUCTS, INC., Plainville, CT (US)

(72) Inventors: Edward De Mayo, Greenbrae, CA (US); Tim Blackwell, Jupiter, FL (US)

(73) Assignee: INNOVATIVE MEDICAL PRODUCTS, INC., Plainville, CT (US)

( * ) Notice: Subject to any disclaimer, the term of this patent is extended or adjusted under 35 U.S.C. 154(b) by 536 days.

(21) Appl. No.: 15/131,349

(22) Filed: Apr. 18, 2016

(65) Prior Publication Data
US 2016/0287237 A1    Oct. 6, 2016

Related U.S. Application Data

(63) Continuation-in-part of application No. 15/098,609, filed on Apr. 14, 2016, which is a continuation of
(Continued)

(51) Int. Cl.
| | |
|---|---|
| *A61B 17/02* | (2006.01) |
| *A61B 50/15* | (2016.01) |
| *A61G 13/00* | (2006.01) |
| *A61G 13/10* | (2006.01) |
| *A61G 13/12* | (2006.01) |

(Continued)

(52) U.S. Cl.
CPC ........... *A61B 17/025* (2013.01); *A61B 50/15* (2016.02); *A61F 5/04* (2013.01); *A61G 13/0036* (2013.01); *A61G 13/101* (2013.01); *A61G 13/1245* (2013.01); *A61B 2017/00477* (2013.01); *A61B 2017/0212* (2013.01); *A61B 2017/0268* (2013.01)

(58) Field of Classification Search
CPC . A61B 17/66; A61B 2017/681; A61B 17/025; A61B 2017/0268; A61B 2017/0275; A61B 17/60
See application file for complete search history.

(56) References Cited

U.S. PATENT DOCUMENTS 3,020,909 A * 2/1962 Stevens ............. A61G 13/0036
                                                5/623
4,526,355 A * 7/1985 Moore ............... A61G 13/0063
                                                5/624
(Continued)

*Primary Examiner* — Anu Ramana
(74) *Attorney, Agent, or Firm* — Damian Wasserbauer, Esq; Wasserbauer Law LLC

(57) ABSTRACT

An elevation apparatus, system and method for elevating the patient's limb when using a manual distractor unit is mounted upon a support frame attached to an operating table side rail. A foot strap is attached to the extension apparatus and to the patient's ankle with a patient's knee support pad, extending from the distractor unit, is positioned under the patient's knee to provide traction to the patient's ankle, which is secured to the support frame. The extension apparatus may be formed with a plurality of attachment points for the foot strap so as to provide improved access to the ankle area with advantages of allowing additional types of procedures a surgeon may perform on the patient and/or the ability of the surgeon to access the ankle area and lower leg.

4 Claims, 6 Drawing Sheets

Related U.S. Application Data application No. 13/134,238, filed on Jun. 3, 2011, now Pat. No. 9,314,272.

(51) Int. Cl.
  *A61F 5/04* (2006.01)
  *A61B 17/00* (2006.01)

(56) References Cited

U.S. PATENT DOCUMENTS

| | | | | |
|---|---|---|---|---|
| 5,020,525 A | * | 6/1991 | Ewing | A61F 5/04 602/27 |
| 5,025,802 A | * | 6/1991 | Laico | A61G 13/12 128/875 |
| 5,290,220 A | * | 3/1994 | Guhl | A61F 5/04 128/882 |

* cited by examiner

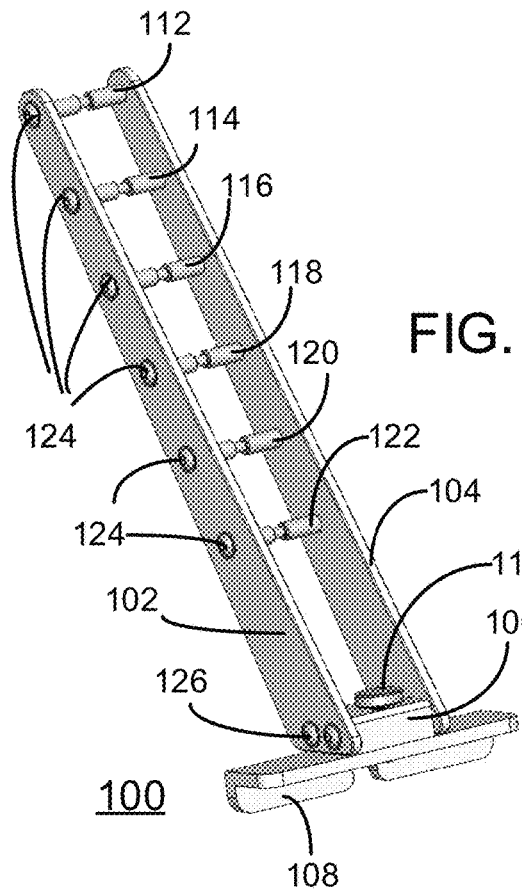
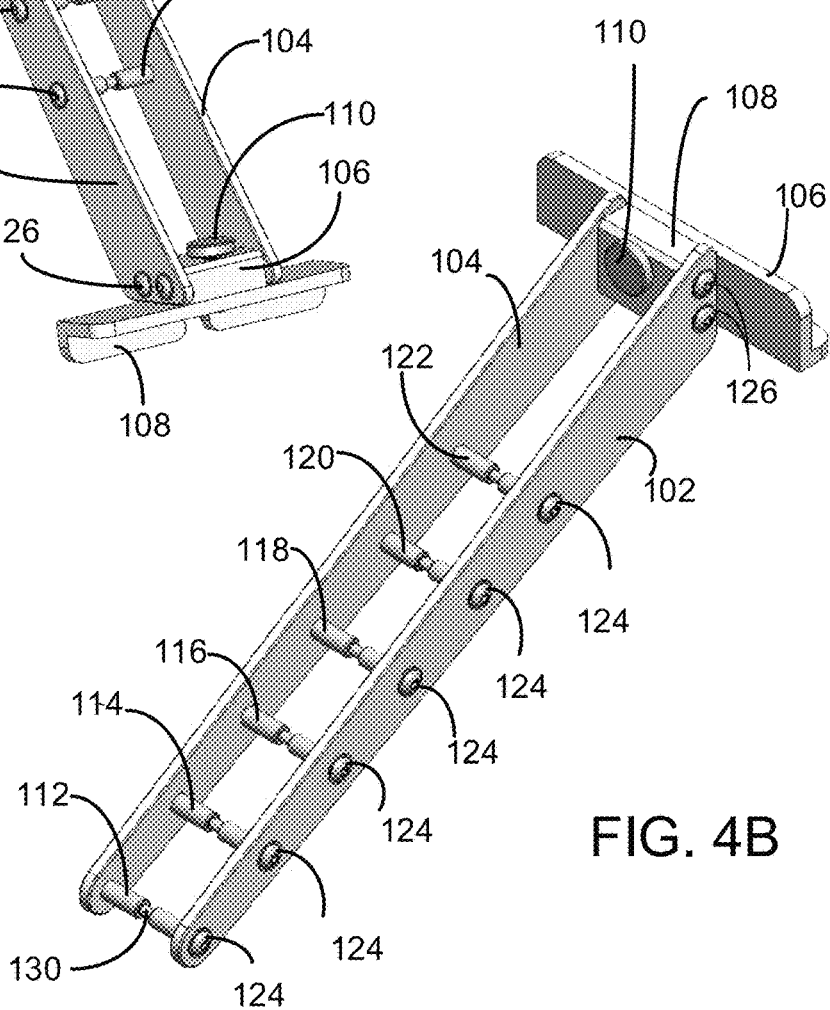

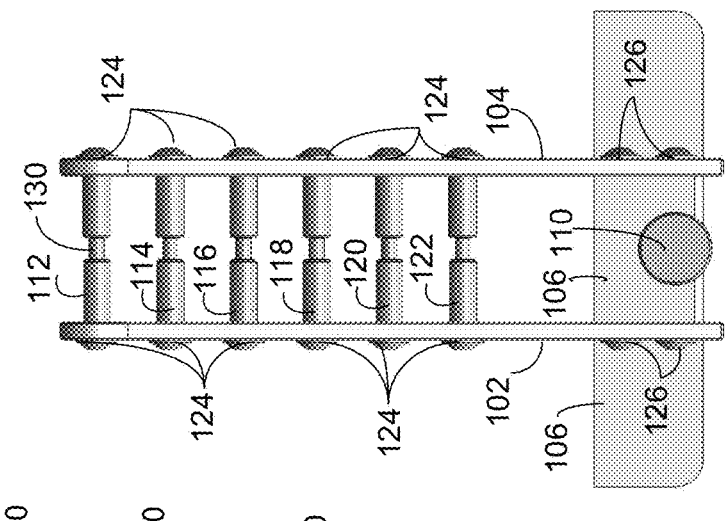
FIG. 6
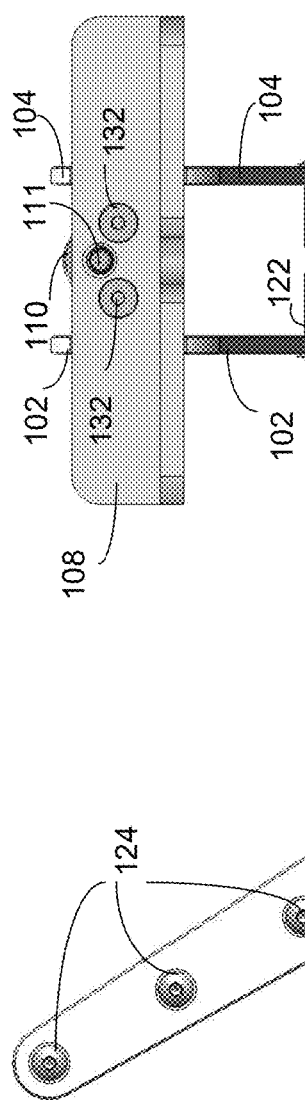
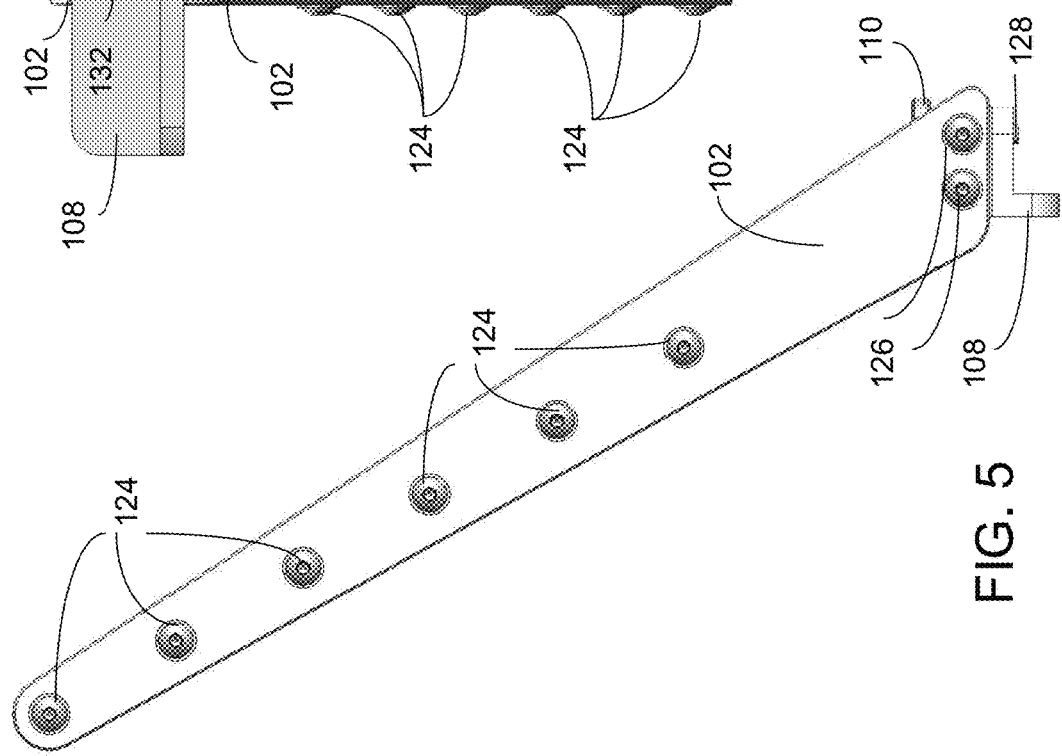
FIG. 7
FIG. 5

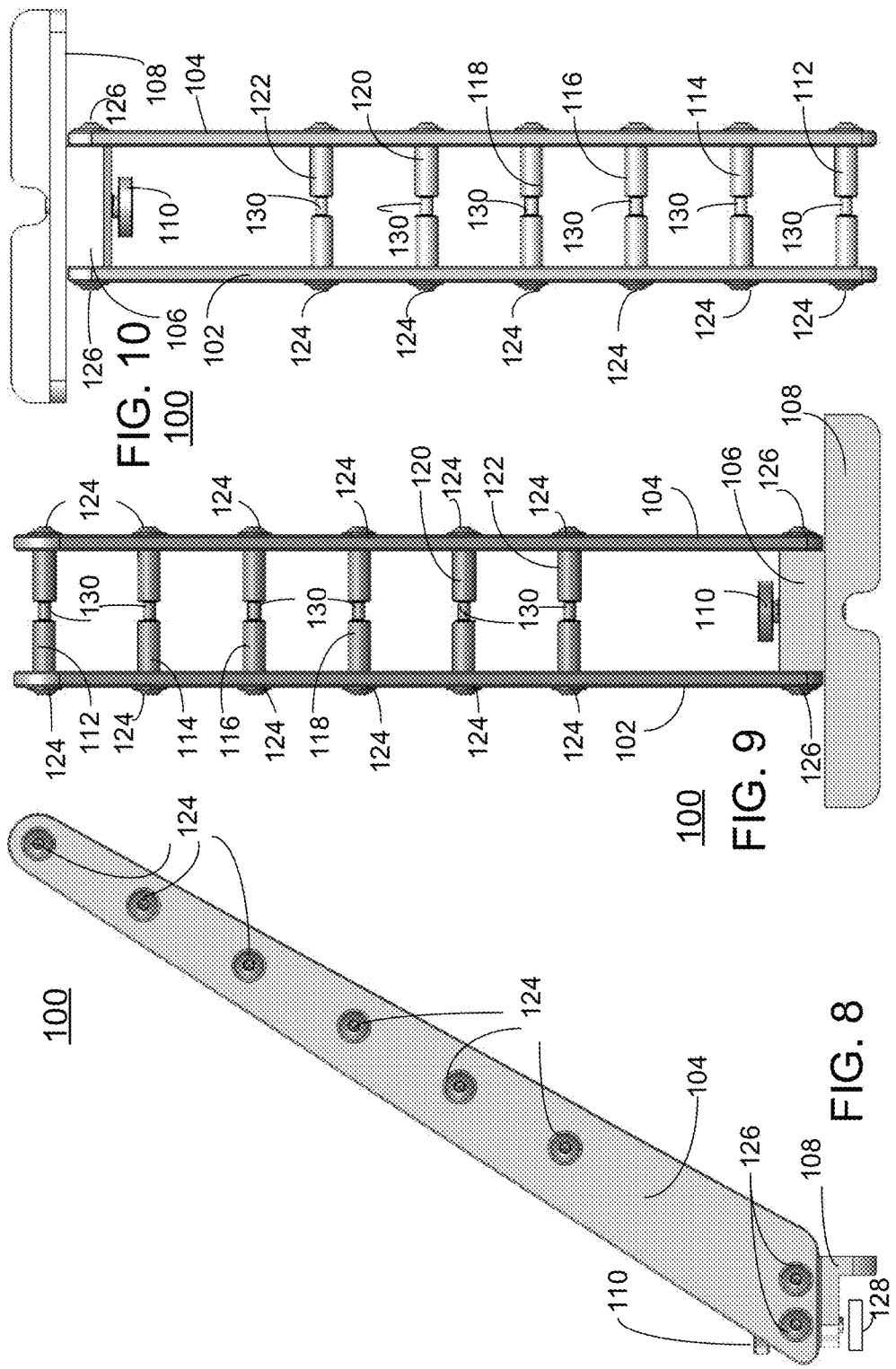

ELEVATION DEVICE FOR MODULAR DISTRACTOR FOR USE IN ANKLE AND LEG SURGERY

CROSS-REFERENCE TO RELATED APPLICATION

This application is a continuation-in-part of U.S. patent application Ser. No. 15/098,609 filed Apr. 14, 2016, entitled "Modular Distractor System For Use In Surgery" which is a continuation of and claims the benefit of U.S. Pat. No. 9,314,272 issued Apr. 19, 2016 entitled "Modular distractor for use in ankle surgery" that are incorporated here by reference in their entirety.

FIELD OF THE INVENTION

The present invention relates to distraction in a surgical procedure and, more particularly, to an elevation apparatus, system and method for holding an ankle and distracting at a knee to provide improved access in surgical procedures involving the ankle area and lower leg.

BACKGROUND OF THE INVENTION

Methods currently available for ankle distraction procedures generally restrain the patient's leg and apply controlled pressure to the ankle for the required traction.

U.S. Pat. No. 5,290,220 entitled "Non-Invasive Distraction System for Ankle Arthroscopy" and U.S. Pat. No. 5,025,802 entitled "Surgical Holding Apparatus for Distracting Ankle" both describe applying such traction to the ankle directly.

The use of such equipment in the vicinity of the ankle could impair circumferential access to the patient's foot and ankle, during surgery, under some circumstances.

It has been shown that by restraining the patient's ankle with a simple strap and applying pressure to the underside of the patient's knee, the ankle can be distracted while allowing the surgeon complete access to the ankle in all directions.

One purpose of the instant invention is to provide a simple means of securing the patient's ankle while applying pressure to the underside of the patient's knee for such ankle arthroscopy by means of a manual distractor which can also be used for other joint arthroscopic surgery.

SUMMARY OF THE INVENTION

One end of a manual distractor unit used in various joint distraction surgery is mounted to one end of a support frame attached to an operating table side rail. A patient's knee support pad, at an opposite end of the distractor unit, is positioned under the patient's knee to provide traction to the patient's ankle, which is secured by a strap to the support frame.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Description of the Preferred Embodiments, which is to be read in association with the accompanying drawings, which are incorporated in and constitute a part of this specification, show certain aspects of the subject matter disclosed herein and, together with the description, help explain some of the principles associated with the disclosed implementations, wherein:

FIGS. 4A and 4B are a perspective views of the elevation assembly according to an embodiment of the present invention;

FIG. 5 is a side view illustrating the elevation assembly according to the present invention;

FIG. 6 is a bottom view illustrating the elevation assembly according to the present invention;

FIG. 7 is a top view illustrating the elevation assembly according to the present invention;

FIG. 8 is a side view illustrating the elevation assembly according to the present invention;

FIG. 9 is a front view illustrating the elevation assembly according to the present invention; and FIG. 10 is a rear view illustrating the elevation assembly according to the present invention.

DESCRIPTION OF THE PREFERRED EMBODIMENTS

Figure 1:
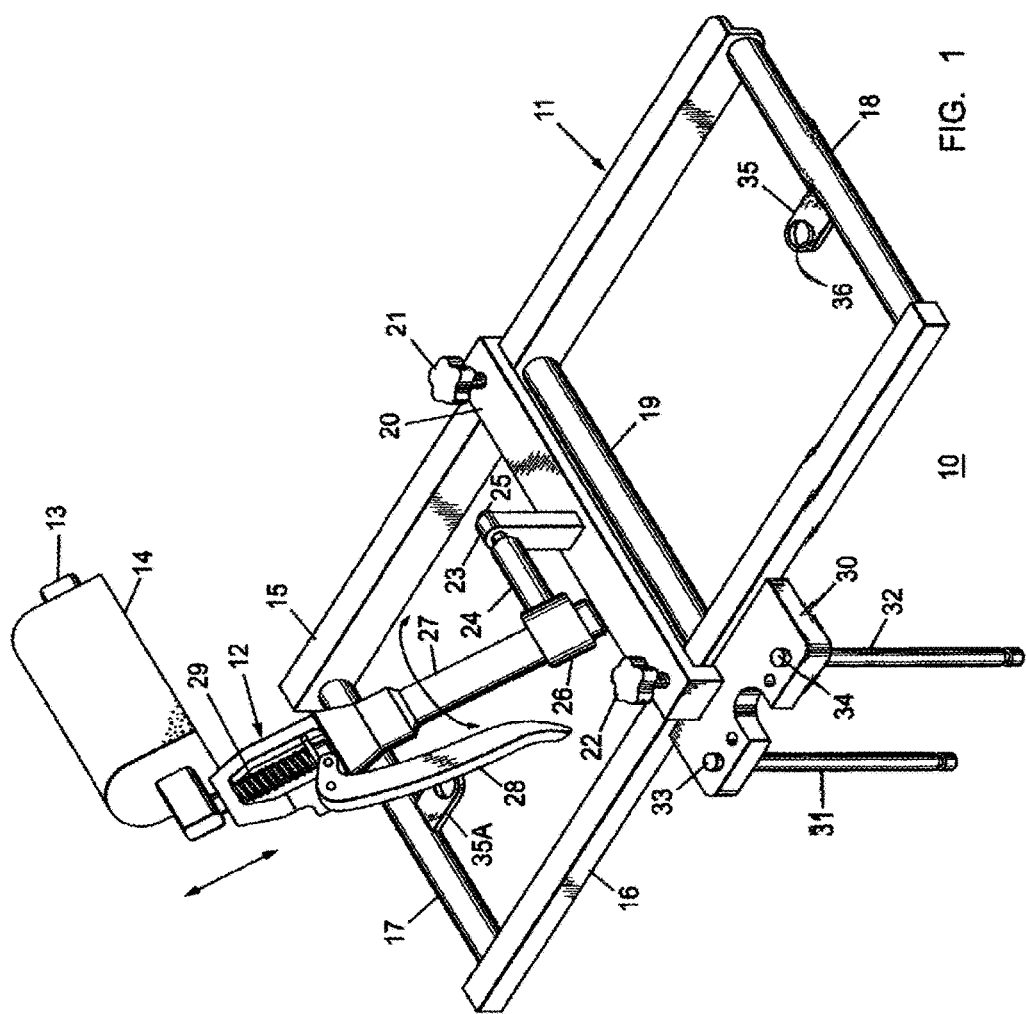
FIG. 1 is front perspective view of the modular patient's ankle distractor unit in accordance with the invention prior to attachment to the operating table.

Non-limiting embodiments of the present invention will be described below with reference to the accompanying drawings, wherein like reference numerals represent like elements throughout. While the invention has been described in detail with respect to the preferred embodiments thereof, it will be appreciated that upon reading and understanding of the foregoing, certain variations to the preferred embodiments will become apparent, which variations are nonetheless within the spirit and scope of the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are provided for the purposes of illustrating some embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein the term "elevation" refers to the height to which a structure is being projected geometrically on a vertical plane parallel to one of its sides of the support frame, support table, the operating table, or other base plate from which the attachment point for the tabs or recess for attaching the foot strap are elevated something is elevated or to which it rises above the operating table.

Referring to FIGS. 1 through 10, an elevation apparatus, system and method 100 for use with the ankle distractor and strap for restraining the patient's ankle with a simple strap attached to the extension apparatus 100 and to the patient's ankle while applying pressure to the underside of the patient's knee by an distractor assembly 12 for improved access to the overall leg including the ankle for during arthroscopic surgery or other surgical procedure at the ankle and tibia area.

Figure 2:
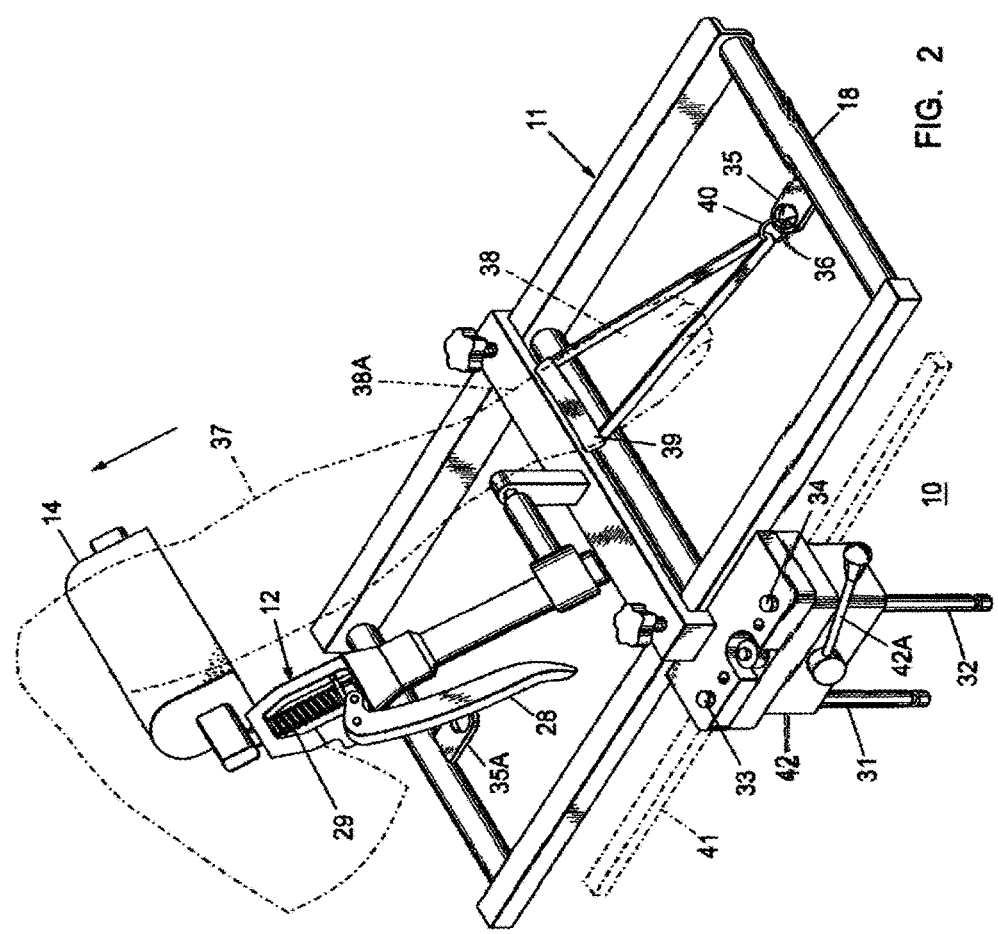
FIG. 2 is a front perspective view of the patient's ankle distractor unit of FIG. 1 after attachment to the operating table with a portion of the patient's limb depicted in phantom thereon.
Figure 3:
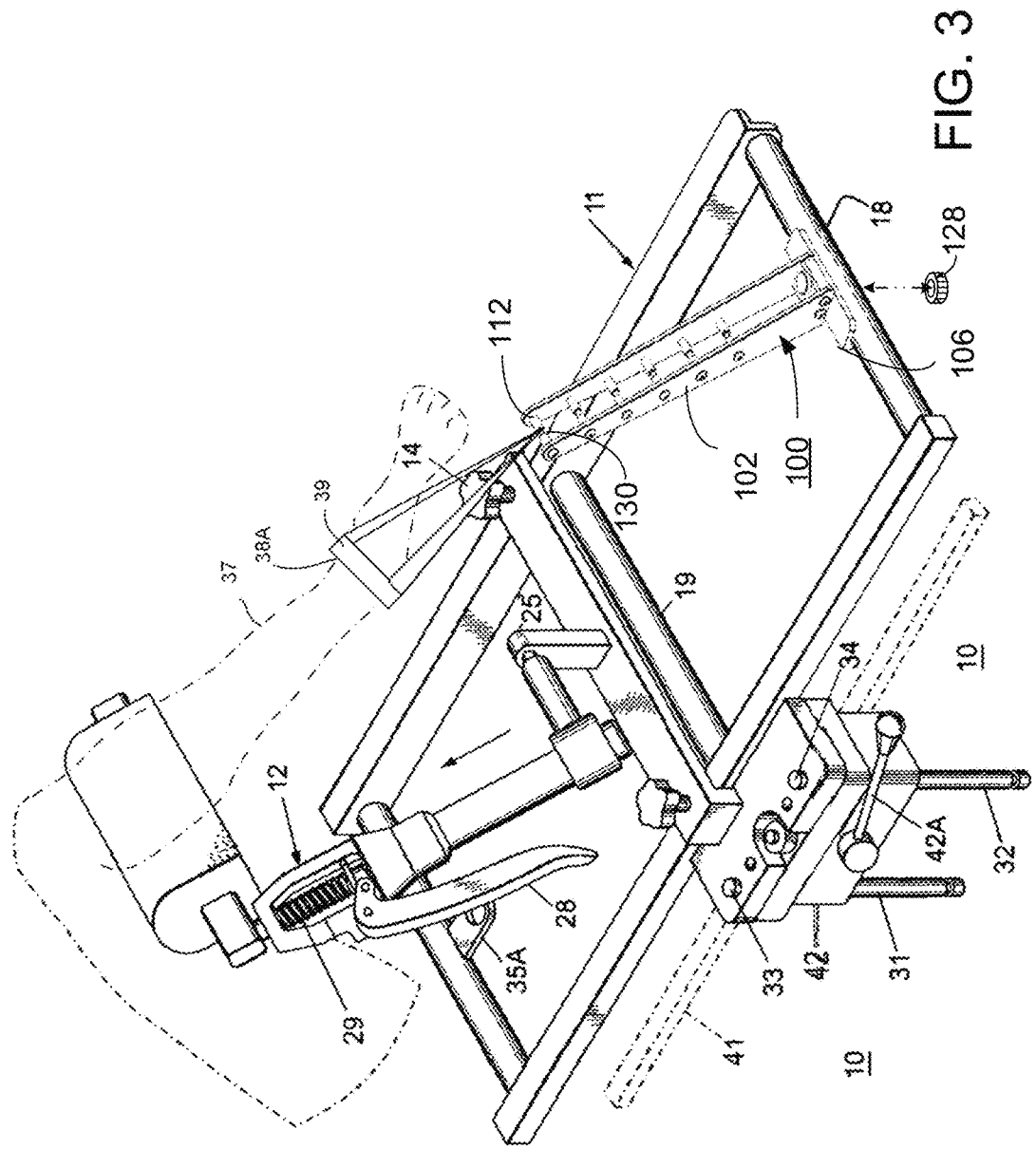
FIG. 3 is a side perspective view of the elevation assembly after attachment of the support frame to an operating table shown in FIG. 1 for surgical procedures involving the lower limb, tibia, or ankle surgical procedures with a portion of the patient's limb depicted in phantom thereon according to an embodiment of the present invention.

Referring to FIGS. 1, 2 and 3, the elevation apparatus, system and method 100 comprises a pair of elongated, upwardly extending side plates 102 and 104 that are secured to a mounting block 106 and are secured to the support frame 11 through a base bracket 108 and fastener means utilizing the e-stop 110. The e-stop 110 may be configured with a threaded post 111, as shown in FIG. 6, for connecting to a tab 35 by suitable tab fastener 128 and/or incorporated as a threaded hole 36 of the support frame 11, for example, as is illustrated in FIGS. 3, 6, and 8. As illustrated in FIGS. 4A-4B, and 5-10, A plurality of mounting rods 112, 114, 116, 118, 120, and 122 are disposed between the side plates 102 and 104 so as to provide multiple attachment points for the foot strap 39. Advantageously, the plurality of mounting rods 112, 114, 116, 118, 120, and 122 include a strap recess 130 configured to receive a hook, ring, tape, fabric, rope or other extension of the foot strap 37 so as to center between extending side plates 102 and 104.

As illustrated in FIGS. 4A through 10, a plurality of rod fasteners 126 may be used to secure the mounting rods 112, 114, 116, 118, 120, and 122 to the side plates 102, 104. In an alternative embodiment, the mounting rods 112, 114, 116, 118, 120, and 122 to make be connected to the side plates 102, 104 by welding, adhesives, or other attachment methods. And still yet another embodiment of the present invention, the mounting rods 112, 114, 116, 118, 120, and 122 to make be connected to the side plates 102, 104 may be formed from a solid material such as surgical stainless steel by computer numeric controlled (CNC) milling techniques. The components of the side plates 102, 104, a mounting block 106, base bracket 108, and the plurality of mounting rods 112, 114, 116, 118, 120, and 122, may be formed from suitable materials such as surgical grade stainless steel, and other metal alloys.

As shown in FIGS. 1-3, a modular ankle distractor unit 10 includes a support frame 11 and a manual distractor 12, which includes a support bar 13 for the patient support pad 14 for moving the support pad 14 in the up and down directions, as indicated, in combination with the compression spring 29 and the distractor operating handle 28. The manual distractor 12 is described within U.S. patent application Ser. No. 12/001,194 entitled "Non-Invasive Femoral Distractor," which Application is incorporated herein for purposes of reference.

The support frame 11 includes a pair of side bars 15, 16, end bars 17, 18 and center bar 19. A support bar 20 extends between the side bars 15, 16 and is attached thereto by means of threaded knobs 21 and 22. A post 23, upstanding from the support bar 20, is attached to a rod 24 by means of a bolt 25 and the rod 24 is welded to the support collar 26. One end of the manual distractor cylinder 27 is arranged within the support collar 26 whereby the manual distractor 12 can be rotated in the clockwise and counter-clockwise directions, as indicated, by loosening the bolt 25. The plate extension 30 on the end of the support bar 20 includes at a pair of operating table connector posts 31, 32 attached thereto by means of bolts 33 and 34. A tab 35 is attached to the end bar 18 and includes an opening 36 for receiving a clip connector 40 to retain the patient's foot strap 39, as shown in FIG. 2. A similar tab 35A is attached to the end bar 17.

Referring now to FIGS. 2-3, the support frame 11 is depicted attached to an operating table side rail 41 by a side rail clamp 42 and operating handle 42A which engages the operating table connector posts 31, 32. The side rail clamp 42 is similar to that described within U.S. Pat. No. 7,380,299 entitled "Operating Table Support Clamp". To provide ankle distraction, a patient's limb 37 is arranged on the patient support pad 14 and the patient's foot 38 is secured within foot strap 39, which is secured to the end bar 18 by means of the tab 35, clip connector 40 and opening 36, as described earlier. One such foot strap 39 is a Guhl Ankle Distractor Foot Strap obtained from Smith & Nephew Inc. To provide distraction to the patient's ankle 38A, the distractor operating handle 28 on the manual distractor 12 is operated to move the patient support pad 14 and limb 37 in the indicated direction, while the ankle 38A is retained by virtue of the foot strap 39. When the distraction of the ankle 38A is completed, the compression spring 29 allows the support pad 14 to return the limb 37 to the original position upon release of the distractor operating handle 28.

A simple and efficient arrangement has been described herein whereby a patient's ankle can be precisely distracted by use of a manual distractor that is used for other limb distraction as well. Referring to FIG. 3, certain circumstances require the patient's leg to be positioned differently so as to access the entire limb leg and the ankle area. As a result, the present invention provides an elevation assembly, system and method 100 that may be secured to the frame 11. The elevation assembly 100 is configured to distract at the knee with the limb being positioned at different horizontal angles with respect to the table so as to accommodate the exact position the surgeon has to place the patient in based on the various factors such as, for example the type of fracture, the type of surgery, the type of arthroscopic surgery, patients body and/or limb size with multiple attachment points for the strap 37. For example, in a surgical procedure to reset a tibial fracture with distraction at the knee by the manual distractor unit 12, or to strengthen the tibial fracture with surgical plates and pins, the elevation assembly 100 may be used to position the patient's limb substantially horizontal so as to provide improved access for the surgeon. Similarly, in surgical procedures for the ankle area, the elevation assembly may be utilized to position the limb in various relative horizontal position so as to properly position the ankle according to the fracture and other factors for improved access to the ankle area when the ankle area is distracted.

In many surgical procedures, this arrangement is adequate to address and have access to the patient's leg area in arthroscopic surgeries and fractures as well as improved access to the area of the ankle. Referring to FIG. 2, according to an embodiment of Applicant's invention, an ankle distractor and strap, system and method is used for restraining the patient's ankle with a simple strap and applying pressure to the underside of the patient's knee, the ankle can be distracted while allowing the surgeon complete access to the ankle in all directions. Such an ankle distractor and strap is described in U.S. patent application Ser. No. 13/134,238 filed Jun. 3, 2011 entitled "Modular distractor for use in ankle surgery," which is incorporated by reference herein in its entirety.

While certain configurations of structures have been illustrated for the purposes of presenting the basic structures of the present invention, one of ordinary skill in the art will appreciate that other variations are possible which would still fall within the scope of the appended claims. Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A modular distractor system for use in distraction surgery on the leg of a patient, comprising:
   a support frame comprising a pair of first and second side bars, a pair of end bars, a support bar operably connected between said first and second side bars, a post extending from said support bar operably connected to a support collar, and a plate extension operably connected to said support bar, said plate extension comprising a pair of connector posts for operably connecting to a side rail clamp attached to the operating table,
   a manual distractor unit comprising a collar portion at one end configured to operably connect to said support collar of said support bar and an adjustable assembly at an opposite end comprising a support bar configured to receive a support pad, a distractor handle and a compression spring, said adjustable assembly configured to move said support pad in combination with a distractor handle and a compression spring, said collar portion configured to provide rotatable adjustment of said manual distractor unit relative to said support frame, said support pad adapted to apply pressure to the popliteal area of a patient's knee when said adjustable assembly unit is extended linearly, said compression spring for moving said support bar thereby returning to an original position after the distraction has been completed;
   a foot strap for securing a patient's ankle and/or foot; and
   an elevation assembly operably connected to one of said pair of end bars of said support frame, said elevation assembly comprising elongated, upwardly extending side plates supporting a plurality of mounting rods for attaching said foot strap thereto.

2. The distractor system of claim 1, further including a recess formed in each of said plurality of mounting rods for holding said foot strap at a central portion of said plurality of mounting rods between said side plates.

3. The distractor system of claim 1, further comprising a mounting block and a base bracket for securing said elevation assembly to said support frame, and an e-stop for securing to a tab located on one of said pair of end bars of said support frame.

4. The distractor system of claim 3, wherein said, said e-stop is configured with a threaded post for connecting to said tab by a fastener and/or by a threaded hole in one of said pair of end bars of said support frame.

* * * * *